United States Patent [19]

Krongrad

[11] Patent Number: 5,786,362
[45] Date of Patent: Jul. 28, 1998

[54] METHOD OF TREATING HORMONE INDEPENDENT CANCER

[75] Inventor: Arnon Krongrad, Surfside, Fla.

[73] Assignee: University of Miami, Miami, Fla.

[21] Appl. No.: 260,884

[22] Filed: Jun. 16, 1994

[51] Int. Cl.⁶ .................................................. A61K 31/44
[52] U.S. Cl. .................................................. 514/280
[58] Field of Search ........................................ 514/280

[56] References Cited

PUBLICATIONS

Herbert et al., Biochem. Biophys. Res. Commun. vol. 172, No. 3, 1990, pp. 993–999.

*Primary Examiner*—Jerome D. Goldberg
*Attorney, Agent, or Firm*—Morgan & Finnegan, LLP

[57] ABSTRACT

Activation of the c-fos promoter and the serum response element (SRE) in androgen independent cancer cells has been demonstrated. In androgen dependent cells, direct activation of protein kinase C (PKC) or serum response factor (SRF) activated the c-fos promoter or SRE and caused androgen independent expression of an androgen target promoter. The highly specific PKC inhibitor chelerythrine selectively killed androgen independent cells. Expression of mutant SRF cDNA's inhibited activation of the SRE in prostate cancer cells. These reagents demonstrate the feasibility of both chemotherapy and gene therapy in interfering with intracellular pathways on which androgen independent cells are dependent; i.e. a strategy is outlined for treating hormone independent cancer in which the PKC-SRE pathway is disrupted by either chemotherapy or gene therapy.

2 Claims, 4 Drawing Sheets

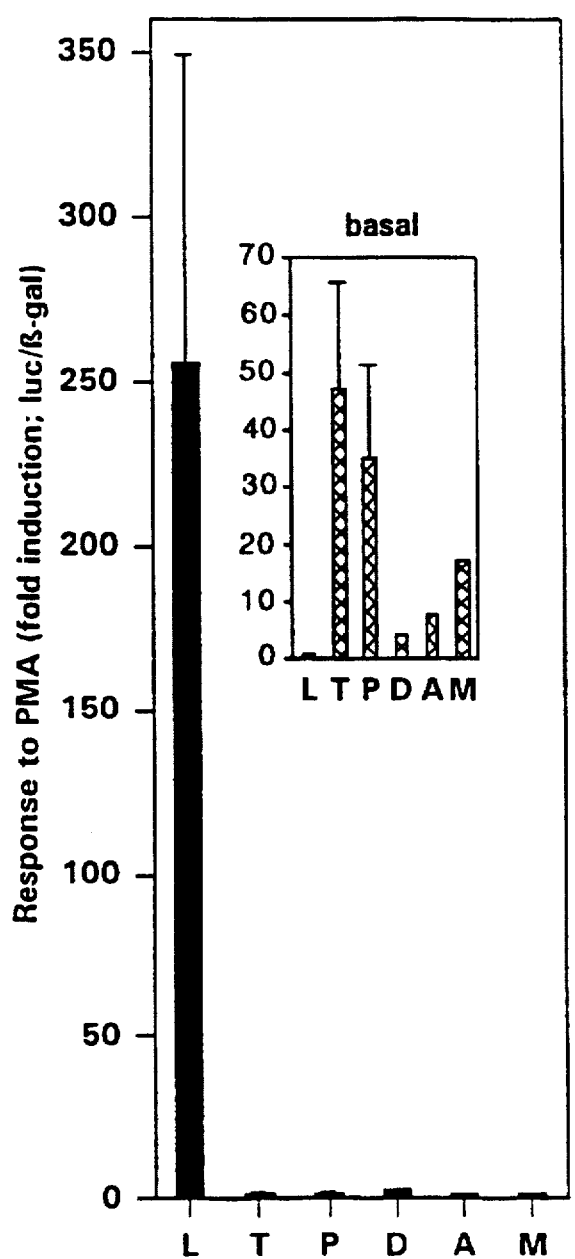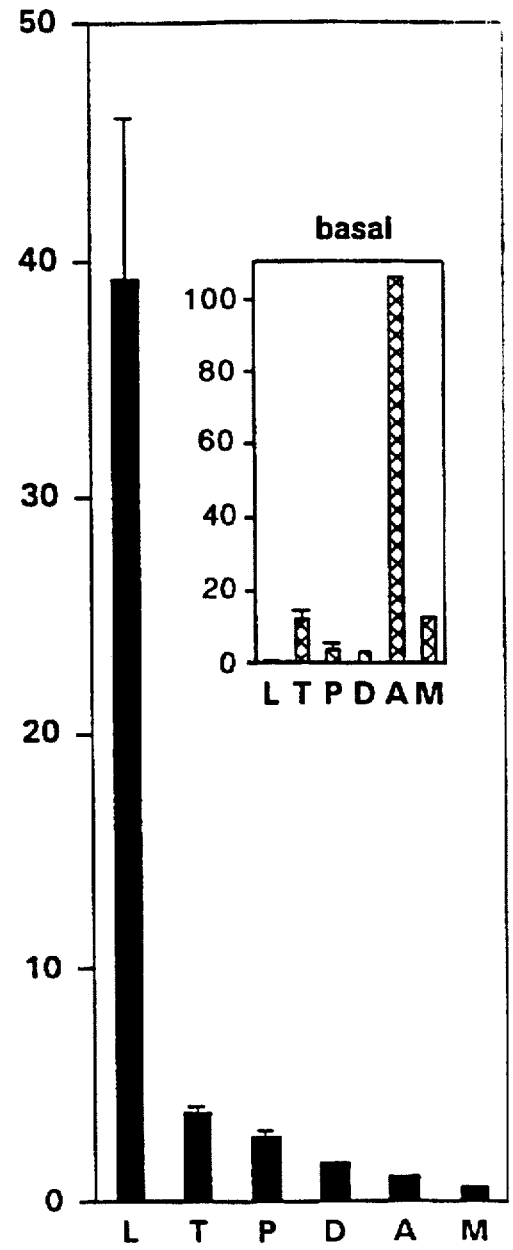

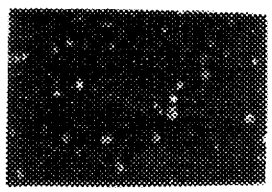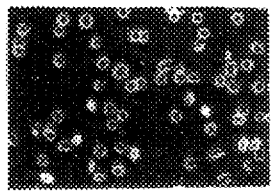
FIG. 4

METHOD OF TREATING HORMONE INDEPENDENT CANCER

FIELD OF THE INVENTION

The invention relates generally to controlling cancer cell proliferation in tumors which are hormone dependent. Specifically it relates to an elucidation of the biological signal transduction necessary for cancer cell proliferation when the cancer cells have become hormone independent, and the determination of means capable of interfering with progression of cancer cell growth or inhibiting cancer cell growth.

BACKGROUND OF THE INVENTION

Cells prioritize responses to concurrent biological signals. With hormonal signals, the manner in which response to hormone is realized depends not only on hormone and receptor, but also on other factors. In the case of nuclear hormone receptors such as the steroid receptors, prioritization of conflicting signals is realized by the relative influence of steroid receptor and nuclear effectors of other signals (reviewed in 1, 2).

Many studies on nuclear signal prioritization have been done in host cells artificially expressing the signal effector of interest, e.g. steroid receptor, components of Ap1, and the like (1,2). How signal prioritization is determined in cells normally expressing these effectors is not well known. For instance, there are biological systems expressing androgen receptor (AR) in which responses to androgens vary markedly. In the prostatic acinus, for example, all epithelial cells from proximal to distal express AR (3), yet some grow, some die, and some differentiate in response to androgen (4,5). Similarly, in epithelial cancers, expression of AR does not predict quality of response to androgen (6). There is little information on what factors other than androgen and AR not only have the ability, but are in actuality differentially determining response to androgens in some cells and not others. Increased growth has been observed in breast cancer cells on evolution to estrogen independence (7,8). This background knowledge led to the present hypothesis by applicant that growth regulated genes are deregulated in androgen independence.

SUMMARY OF THE INVENTION

The present invention relates to the discovery that proliferation of cells of late stage hormone dependent cancers which have become hormone-independent can be selectively inhibited or killed by subjecting cell populations containing such cells to inhibitors of protein kinase C (herein referred to as "PKC"). Applicant has observed that cells in which hormone dependence is lost grow aggressively and relatively independently of serum. In particular, hormone-independent cancer cells can be selectively killed by specific PKC inhibitors, such as, for example, cheleryth-rine.

The present invention relates to a method of treating populations of cells with a PKC inhibitor, such that hormone-independent tumor cells in the cell population are selectively growth inhibited or killed. In addition, the present invention relates to the use of PKC inhibitors as a biological marker of hormone-independence in cancerous cell populations. In particular, the PKC inhibitor, cheleryth-rine is a useful biological marker for androgen-independent cells.

The present invention further relates to the growth inhibition or killing of androgen independent cells wherein the growth-regulated gene c-fos and the serum response element (referred to as "SRE") genetic sequence are deregulated. Direct activation of PKC in androgen dependent cells can mimic the c-fos or SRE deregulation seen in androgen independence and also cause androgen independent expression of an androgen target promoter, probasin. Direct activation of the serum response factor (referred to as "SRF"), the final effector in the PKC signaling cascade, was found to be sufficient to do the same. These discoveries have led, in the present invention, to a new biochemical model of hormone action. Using the predictions made by this model, the present invention has identified a means to selectively growth inhibit or kill hormone-independent cells. In addition, the present experiments have demonstrated the feasibility of utilizing genetic reagents to target components of the signaling pathway so as to allow gene therapeutic approaches to hormone independent cancers. The present invention allows the growth inhibition or killing of tumor cells in a cell population comprising hormone independent cancer cells as to the design of novel therapeutic strategies in hormone independent cancers.

DESCRIPTION OF THE FIGURES

FIG. 1 c-fos promoter or SRE are activated in androgen independent cells. Each graph represents a composite of experiments in which each androgen independent line was compared to the androgen dependent LNCap used as an internal control. Solid bars represent mean fold induction by phorbol ester, normalized to expression of the reporter in the same line in the absence of phorbol ester. Hatched bars in the inset represent relative basal expression of the reporters normalized to the basal expression of that report in LNCap in the absence of phorbol ester. In the insets, basal expression of each reporter in L has a value of 1. In panel a, _____, T, P, D, A, and M were tested 8, 3, 5, 1, 1, and 1 time error bars represent standard error. In panel b, L, T, P, D, A, and M were tested 3, 3, 3, 1, 1, and 1 time each error bars represent standard error. L=LNCap, T=TAC, P=PPC-1 (clone 11), D=DU145, A=ALVA-31, M=MFM-M.

FIG. 4 PKC inhibitor chelerythrine selectively kills androgen independent cells. Cells were plated at subconfluence in 1% DCSS with or without 5 μM chelerythrine.

DETAILED DESCRIPTION OF THE INVENTION

Figure 2A:
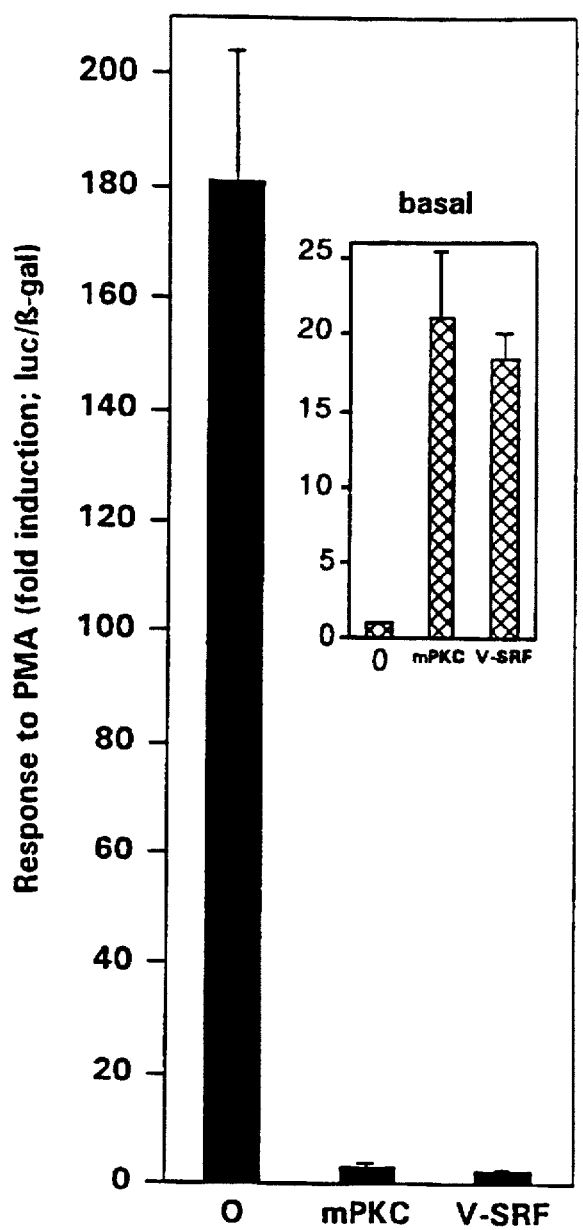
FIG. 2 Expression of activated PKC or VP16-SRF activates c-fos promoter or SRE. Cells were then treated as described in the legend to FIG. 1. Error bars represent standard error. Bar designation is as in FIG. 1. Each experiment was done three times. Paired student t-test was used to detect significant differences in experimental results, using SigmaPlot for Windows computer software (Jandel Scientific, San Rafael, Calif.).

Differential hormone action is determined partly by regulation of hormone receptor. However, factors other than receptor also critically determine biological responses to hormone. In the prostatic acinus, for example, all epithelial cells express androgen receptor (AR-3), yet some grow, some die, and some differentiate in response to androgen (4,5). Similarly, in epithelial cancers, expression of AR does not necessarily predict quality of response to androgen (6). This is problematic in the clinical management of diseases such as prostate cancer in which changes in androgen action signifies endstage disease—biological or chemical markers of differential androgen action would be useful in targeting therapies. There is little information on cellular factors other than AR which differentially determine discrete biological responses to androgens. Previously cells in which the growth response to androgens has been lost have been observed to grow relatively independently of serum. Increased growth has also been observed in breast cancer cells on evolution to estrogen independence (7,8). This led to the hypothesis that growth regulated genes are activated in androgen independence and that understanding this putative relationship might lead to better markers of differential androgen action.

Growth-related activation of c-fos can be mediated by the SRE (13,14). Initial tests of the hypothesis focused on c-fos, a gene whose regulation in growth stimulation by serum or phorbol esters has been well characterized (9–11). Initial experiments were done using a 700 bp "full-length" c-fos promoter construct which includes many functional response elements (12). The SRE genetic sequence is also found in other growthregulated genes (15–17) and is necessary for activation of c-fos by phorbol esters (18), but may be activated by a variety of signals (19–22). Activation of the SRE may occur with transactivation of a constitutively bound protein, the $p67^{SRF}$, a.k.a. the serum response factor ("SRF":23). However, loss of SRF binding to the SRE can also lead to activation of the c-fos promoter through activation of adjacent sequences (24). In other words, high basal activity of full length c-fos promoter associated with non-inducibility by phorbol esters in androgen independence could in theory be explained by activation of the SRE or of adjacent sequences.

The SRE is classically thought to be activated by signaling pathways mediated by PKC. However, SRE activation may also occur through non-PKC dependent pathways (19–22). Tests have been conducted to determine if direct (without use of phorbol ester) PKC activation could be causally linked to c-fos or SRE activation (see example 2). To effect direct activation of PKC, a mutant PKC (mPKC) plasmid in which the coding sequences were mutated to interfere with the function of the autoinhibitory pseudosubstrate region, thus raising enzymatic activity (25) was utilized. As an added comparison, the ability of activated serum response factor (SRF) to activate the c-fos promoter or SRE was also tested. The SRF was selected because it is thought to mediate PKC action at the SRE (20), and might in fact be the final effector of the PKC signaling pathway (23). It is thought that the SRE is both necessary and sufficient for SRF transactivation of the c-fos promoter (26). The activated SRF plasmid, VP16-SRF, is a chimeric construct in which the phosphorylation dependent transactivation domain was replaced by the constitutively active VP16 viral transactivation domain (27).

Given that activated PKC or SRF were sufficient to reproduce a specific characteristic of androgen independent cells, SRE activation, the present invention also examined whether such activation could suffice to reproduce the primary characteristic, independence from androgens. To test this, the expression of probasin promoter in response to a synthetic androgen, mibolerone, was examined (see example 3). The probasin gene codes an androgen-dependent prostate-specific secretory product, whose promoter contains well-characterized androgen response sequences (28) and was rendered androgen independent with mutant PKC and SRF.

The phorbol ester insensitivity seen in the androgen independent cells (example 3) is reminiscent of what is seen with chronic phorbol ester stimulation (29). In this situation, long-term phorbol ester, classically thought to act through PKC (30), reduces cellular responses to more phorbol ester. The possibility that PKC activity may be of relative biological significance was supported by the observation that PKC activation could reproduce the two primary characteristics of the androgen independent cells, activation of the SRE and relatively androgen independent regulation of an androgen target promoter. To indirectly test the possible biological significance of PKC activity in androgen independence, cells were incubated with the highly specific PKC inhibitor chelerythrine (31,32).

Figure 3:
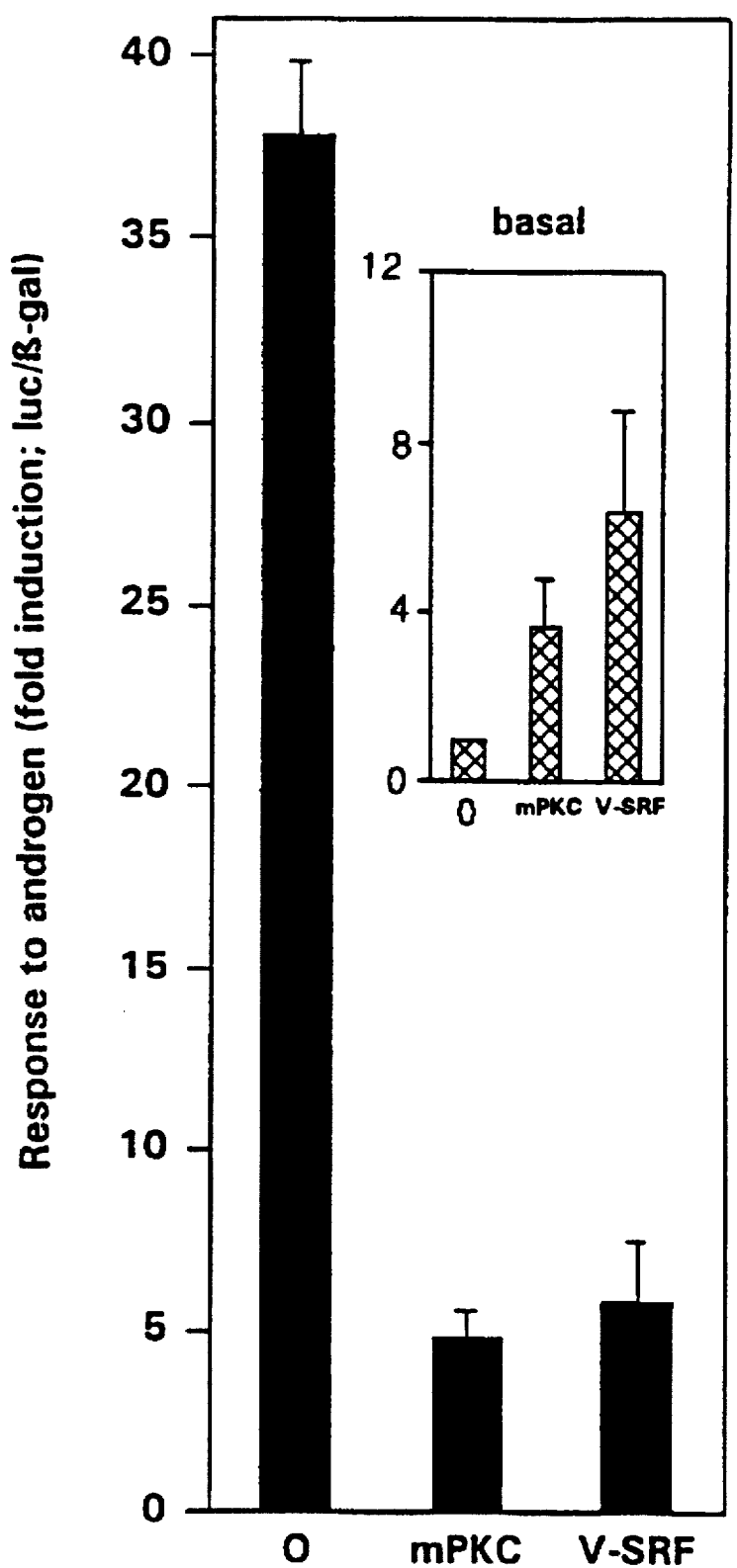
FIG. 3 Expression of mutant PKC or VP16-SRF is sufficient to abolish probasin promoter induction by androgen. Error bars represent standard error and bar designation is as in FIG. 1. The experiment was done four times.

The morphology of the androgen dependent cells LNCap and ZR-75-1 was unaffected by chelerythrine concentrations of $\leq 10 \mu M$. By contrast, the androgen independent cell lines exhibited dramatic morphological responses to chelerythrine at concentrations $\leq 5 \mu M$. Specifically, the androgen independent cells TAC, PPC-1, DU15, ALVA-31, and MFM-M became rounded and granulated and detached from the culture dish. The medium in which the androgen independent cells were grown filled with cell debris. These findings were interpreted to represent inhibition of growth and proliferation, and cell death. (FIG. 3). This provides indirect evidence that PKC activity is of relative importance in the viability of androgen independent cells but not androgen dependent cells. The cell death response to chelerythrine, occurs in cells whether or not the cells express the androgen receptor. Thus, an assay which selectively inhibits or kills hormone independent cancer cells can be useful as biological marker of hormone-independent cell growth in such tumors.

The present invention demonstrates that PKC inhibitors kill androgen-independent cells. In addition, PKC acts through SRE. The SRE is presently shown to be activated in androgen-independent cells. Also, it is be shown that SRE inhibition arrests cell growth (57). Taken together, these findings have led to the discovery of methods for inhibiting SRE either via PKC inhibitors or by directly modulating SRE through SRF.

SRE is potentially important in growth stimulation. This is predicted by the presence of SRE in many growth responsive genes as discussed hereinabove. Direct evidence is provided by the observation that SRF mutants inhibit c-fos induction and DNA synthesis (57). To identify reagents which may allow testing the role of SRE activation in androgen independence, an SRF mutant was selected with altered DNA-binding in the hopes of sequestering necessary cofactors away from the target endogenous SRE's. SRF-M2, a human SRF in which part of the DNA binding domain (amino acids 133–166) had been switched to the yeast MM-CM1 DNA binding domain was chosen (2; gift of Richard Treisman). This mutant does not bind to or activate the mammalian SRE and does not appear to heterodimerize with the wt-SRF (58). It does contain the peripheral SRF domains thought crucial for recruitment of transcriptional cofactors such as Elk-1 (58). Thus,one would predict that SRF-M2 would "squelch" SRE activity by recruiting cofactors to complexes without DNA-binding ability.

Transient expression of SRF-M2 inhibited the activity of SRE (and c-fos promoter) in dose dependent manner. Basal SRE activity was reduced 50% with 10 µg SRF-M2 (relative to basal level with Bluescript cotransfectant). Induction of SRE activity with phorbol ester was reduced 46% with 1 µg SRF-M2 and up to 89% with 20 µg SRF-M2. Thus, this construct may be useful in exploring the biological consequences of SRE inhibition.

Inhibition of the SRE arrests cell growth as can be seen from the discussion, hereinabove. Therefore, it may be impossible to establish clones in which SRE is constitutively inhibited. Thus, there is a need for inducible regulation of SRF-M2.

It will be possible to utilize any reagents developed in the present feasibility studies in biologically more complicated models, including transplanted cancers and transgenic animals. Also, specificity of reagents for SRE and not other endogenous sequences will simplify interpretation of results.

To construct systems in which direct actions in the cancer cells may be distinguished from indirect endocrine or paracrine actions, ecdysone will be utilized as the regulating hormone. Ecdysone is a steroid hormone found in Drosophila and is not thought to be biologically active in humans or other mammals, probably because its receptor ("EcR") is not expressed (59). Also, given that the EcR hormone binding region is relatively dissimilar from that of mammalian steroid receptors (59), mammalian hormones are not especially likely to activate exogenous EcR. This has been partially validated experimentally (60). The EcR appears to function when heterodimerized to the Drosophila ultraspiracle protein ("USP"), a homologue of mammalian RXR transcription regulatory proteins, which may be necessary for expression in some mammalian systems such as CV1 monkey cells (61, 62). However, in human HeLa cells, EcR appears to function without cotransfected USP, suggesting that mammalian homologues may substitute for USP (61). Thus, in selected mammalian systems, expression of EcR may suffice to confer ecdysone sensitive gene regulation.

The ability of transfected EcR to activate ecdysone response elements ("EcRE's") in the prostate cancer lines LNCap and its androgen independent derivative TAC has been tested. In initial experiments using LNCap, using methods described in Example 1, with transfected EcR expression plasmid, applicant was able to induce an EcRE-driven luciferase reporter plasmid 9,600-fold and 55,000-fold with 1 and 10 µM concentrations of the synthetic ecdysone muristerone A, respectively. Given the magnitude of response, reporter plasmid, EcR expression plasmid and muristerone A were reduced to 10 µg, 1 µg and 1 µM respectively. Under these conditions, induction by muristerone A was 4,000-fold in both LNCap and its androgen independent derivative TAC.

This demonstrates the feasibility of using the ecdysone system in controlling genetic constructs in prostate cancer cells for regulating genes. These biological "handles" can be used to drive biologically active genes (other than luciferase) in the clinical manipulation of human disease, such as cancer. With the SRF-M2 used as the biologically active gene, these "handles" can be used to arrest cell growth.

A further aspect of the present invention relates to a method of regulating genes with biological activity through the use of ecdysone receptor, more specifically a method in which the hormonal regulator is ecdysone, such as, for example, the hormonal regulator is muristerone A or synthetic ecdysone. The instant invention further relates to regulating genes with biological activity by use of a receptor which is constructed of elements of the ecdysone receptor and in which the receptor contains the hormone binding domain of the ecdysone receptor. Even more specifically, the receptor contains the DNA binding domain of the DNA binding domain of the ecdysone receptor. The instant method can be employed to regulate various genes including, for example, a method where the regulated gene is the serum response factor (SRF) or the regulated gene is SRF-M2. It is contemplated that the regulated gene is constructed from parts of SRF or the SRF DNA-binding domain or the SRF transacting domain. In a preferred embodiment of the instant invention the regulated genes are targeted to diseases, such as, for example, epithelial cancer, prostate cancer, or breast cancer. The present method can be practiced such that the regulated genes are driven by ecdysone response elements and in which the ecdysone receptor is supplemented with ultraspiracle or its derivatives (61 & 62).

Contemporary models of androgen action invoke an important role for the androgen receptor (AR). Appropriately, attention has focused on AR in abnormalities of androgen action. In the case of congenital androgen resistance, functionally significant mutations of the AR have been described (33), giving rise to a genetic model of this disease. In androgen independent cancer, however, no consistent pattern of AR expression or mutation has been described (34–42). Thus, genetic models of androgen independent cancer have not emerged.

Cellular growth is known to cause expression of a defined set of genes, including so-called primary response genes (12). Some of these may interact with steroid receptor including androgen receptor and in the process alter response to androgen (2,43). The present invention proposes that, irrespective of androgen receptor expression, androgen independence is characterized by activation of at least some growth related genes. c-fos was selected for testing the hypothesis because in many cell types its expression is considered a marker of growth. In keeping with the hypothesis, c-fos promoter activity was higher in androgen independent cells, and was also less inducible by phorbol esters, i.e. c-fos promoter was activated in androgen independent cells.

It was further shown that the primary determinant of phorbol ester response, the SRE, is also activated in androgen independent cells. This is important given that c-fos promoter is inducible through elements other than the SRE (12). The SRE, however, is important not just as a possible correlate of c-fos promoter induction. This element appears to have been highly conserved throughout eukaryotic evolution (44–46) and is found in many growth-related genes (15–17). Its activation, therefore, symbolizes the potential activation of an unknown number of growth-related genes, of which c-fos is one.

Non-inducibility of c-fos has been described in various biological states (reviewed in 24,47). The possibility was chosen that non-induction by phorbol ester is due to activation of phorbol ester signaling pathways, including PKC, in the androgen independent cells. When phorbol esters are chronically administered to cells, the result may be protracted activation of PKC, down-regulation of certain PKC isoforms, and growth abnormalities and tumorigenicity (48, reviewed in 30,49). In a condition known as desensitization, stimulation with phorbol ester leads to a state in which acute phorbol ester stimuli are ineffective in generating gene response (50,51). This appeared identical to what was seen in the androgen independent cells. There has been no previous link of androgen independence with phorbol ester desensitization. Prior to the present invention, the link of androgen independence to PKC activity was similarly obscure. There is one report of reduced PKC activity in androgen independent cells following inhibition of growth with a progestational steroid (52). There was no evidence, however, that this activity was specific for the androgen independent phenotype, nor was there evidence that it was associated with phorbol ester insensitivity, or was of biological significance.

PKC can activate many cellular pathways and can in fact activate other signals, such as those mediated by cAMP (53). Because this may lead to activation of genes such as c-fos by genetic elements other than SRE (12), complex promoter responses to PKC activation do not necessarily represent activation of SRE. Furthermore, one could not ascertain from activated PKC experiments which cellular events other than activation of SRF, which is thought to be the final effector in the PKC signaling cascade, might be necessary to affect induction by phorbol ester. To address this, an activated SRF was utilized. As demonstrated, either activated PKC or SRF is sufficient to activate c-fos or SRE. Importantly, in prostate cancer cells, SRE activation may not depend on events more proximal in the phorbol ester signaling cascade than activation of SRF.

One of several known androgen target genes, probasin, was utilized to determine if activation of PKC or SRF could also produce independence from androgens, at least as measured by regulation of a specific androgen target gene. As shown, either activated PKC or SRF could render its expression independent of androgen. This demonstrates that some of the factors which can activate the SRE can also produce androgen independence. It is not yet known if this gene-specific relative androgen independence represents a global cellular independence from androgens.

The information that PKC (or SRF) activation could reproduce two characteristics of the androgen independent cells, SRE activation and relative androgen independence, led us to wonder about the relative biological significance of PKC mediated signals in androgen independence. Incubation of cells with a highly specific PKC inhibitor demonstrated that PKC activity may indeed be of relative significance in the viability of androgen independent cells. The present invention has surprisingly found a means to biologically distinguish between hormone-dependent and -independent cancer cells. That the distinction can be made regardless of androgen receptor expression suggests that the signals which chelerythrine targets may be universally activated in progression to androgen independence. Cell death in response to chelerythrine, along with activation of the SRE, represents the first biological marker of androgen independence.

The PKC inhibitors useful in the present invention include inter alia specific PKC inhibitors, such as chelerythrine, calphostin C as well as non specific PKC inhibitors, such as staurosporine, H7 and gossypol.

The present invention relates to a method selectively inhibiting growth or proliferation of hormone independent cancer cells in a cell population wherein the method comprises the deregulation of SRE. More particularly, the method of selectively inhibiting growth or proliferation comprises use of a mutant SRF, which results in altered binding and inhibition of activation of SRE.

It is thought that the mitogenic response of prostate epithelium and epithelial cancer to androgens is indirectly mediated by paracrine growth factors (54,55). It has been indirectly shown that androgen independent cancer cells may selectively express biologically significant PKC activity, which in other systems may reduce cellular requirements for growth factors (56). This suggests a possible model of prostate epithelial growth adaptation to androgen withdrawal, in which biologically significant PKC activation occurs independently of androgen mediated paracrine factors. In other words, in androgen-dependent prostate cancers, androgen regulated paracrine signals would stimulate growth in association with PKC activation.

In hormone-independent cancers, the cells would become autonomous of the hormone-regulated paracrine factors, partly through the increased significance of PKC activity. Whether this would happen through PKC mutation or changes in intracellular signaling is unknown. It is quite possible that the PKC enzymes would be uninvolved in the progression to hormone independence and that, in fact, other factors in their signaling cascade would account for biological independence from hormones. It is notable in this regard that direct activation of the SRF, through which PKC activates the SRE, was sufficient to cause phenotypic responses seen in hormone-independent cancer cells or in PKC transfected androgen-dependent cells.

It is believed that, whether initiated upstream or downstream of PKC, the progression to hormone independence is marked and may be caused by activation of the SRE. This would then be associated with activation of an SRE-driven class of genes, which would cause growth independently of hormones, and regardless of hormone-receptor expression. Exploration of the relationships between PKC, SRE, and hormone mediated growth as described by the present invention are directly related to the development of novel therapeutic strategies for hormone independent cancers.

The present invention generally relates to a method of selectively inhibiting growth or proliferation of hormone independent cancer cells in a cell population wherein a cell population containing hormone independent cancer cells with an effective amount of at least on protein kinase C activity inhibiting agent. Typical PKC activity agents are known to those skilled in the art and include, inter alia, chelerythrine, calphostin C, staurosporme, H7 and gossypol, and the effective amount is that amount which inhibits PKC activity. Such effective amounts are generally known and dependent upon the cell population which is to be treated. Determination of the effective amount in any particular instance or for any specific cell population or hormone independent cancer cell population is determinable without any undue amount of experimentation.

The hormone independent cancer cells which can be growth or proliferation inhibited by the instant method include all cancer cells which were originally hormone dependent but which have been hormone independent. Illustrative cancer cells, include epithelial cancer cells, prostate cancer cells, breast cancer cells, uterine cancer cells, ovarian cancer cells, colon cancer cells.

In general, the instant method relates to inhibiting the growth and proliferation of the hormone independent cancer cells which are, inter alia, androgen independent cancer cells, estrogen independent cancer cells, glucocorticoid independent cancer cells, progesterone independent cancer cells, insulin independent cancer cells, or glucagon independent cancer cells.

Additionally, the present invention relates to a method of selectively inhibiting growth or proliferation of hormone independent cancer cells in a cell population wherein the cell population is treated with an effective amount of an agent such that activation of the serum response element is inhibited. Typically inhibitory agents of the SRE are known to those skilled in the art and include, inter alia, mutant SRF, chelerythrine, and YY1, (63) and the effective amounts are generally known and dependent upon the cell population which is to be treated. Determination of the effective amount in any particular instance or for any specific cell population or hormone independent cancer cell population is determinable without any undue amount of experimentation.

The hormone independent cancer cells, which can be growth or proliferation inhibited by inhibition of SRE activation include all cancer cells that were originally hormone dependent but have become hormone independent. Illustrative, but not limiting of such cancer cells are prostate cancer cells, epithelial cancer cells, breast cancer cells, uterine cancer cells, ovarian cancer cells and colon cancer cells. Other such cancer cells will be clear to those skilled in the art.

In general, the instant method relates to inhibiting the growth and proliferation of hormone independent cancer cells which are, inter alia, androgen independent cancer cells, estrogen independent cancer cells, glucocorticoid independent cancer cells, progesterone independent cancer cells, insulin independent cancer cells or glucagon independent cancer cells.

EXAMPLE 1

All cell lines were cultured in 5% $CO_2$ humidified air at 37° C. and routinely incubated in RPMI-1640containing 10% fetal bovine serum (FBS; media culture facility, Sylvester Comprehensive Cancer Center), except for TAC which was grown in 5% FBS. LNCap is an androgen receptor positive (AR+56) human prostate cancer cell line which is highly androgen dependent (64, 65, 66). Sublines of LNCap have been developed for the study of androgen independence (67). One of these, TAC, has lost the androgen growth response (68). This line expresses 200 fmol dihydrotestosterone (androgen) as does the parent line LNCap. AR expression is supported by RNase protection and immunoblots which demonstrate the characteristic AR doublet at 110 Kd; (69). ALVA-31 is a human prostate cancer cell line (70)—the clone in use in the current investigation has lost AR expression as determined by RNase protection and is androgen independent. DU145 is an AR-human prostate cancer cell line and is androgen independent (64). PPC-1 was described as a newly isolated, highly malignant androgen independent human prostate cancer cell line (71, 72), but is now widely believed to be a derivative of the AR-human prostate cancer cell line PC-3 (73). The clone in these investigations is #11, which is a neomycin resistant AR line used as a control in previous studies (Krongrad et al., submitted). MFM-223 is a human breast cancer cell line which is androgen growth dependent and AR positive (74). This line has given rise to AR positive clones which are androgen independent (75). The MFM-M line is an androgen independent clone which was recharacterized at the University of Miami. This clone expresses 20 mol androgen binding/mg protein, and has an immuno-detectable AR protein doublet. ZR-75-1 is an AR positive androgen dependent human breast cancer line (76). This line was not used in transfection experiments because sufficient reporter levels could not be obtained by existing protocols. The LNCap, DU145, and ZR-75-1 are from ATCC. TAC was a generous gift from Carlos Sonnenschein. ALVA-31 was a generous gift from Richard Ostenson. PPC-1 was a generous gift from Arthur Brothman, and MFM-M was a generous gift from Reinhard Hackenberg. For transfection experiments, $4 \times 10^6$ cells were transfected per data point. Cells were transfected simultaneously with 30 g c-fos promoter (a) or the $SRE_2$-basic (b) plasmid and 3 g of CMV-driven β-galactosidase plasmid used to normalize for transfection efficiencies. Following a two day incubation in 1% dextran-charcoal stripped serum (DCSS), the cells were stimulated for 3 hours with PMA (50 mg/ml), with the control dishes receiving ethanol only. Luciferse activity was expressed as arbitrary light units and normalized to β-galactosidase activity expressed as absorbance (FIG. 1).

Phorbol 12-myristate 13 acetate (PMA) was purchased (Sigma, St. Louis, Mo.) and dissolved for experiments in ethanol. Equal volumes of pure ethanol was used in control dishes. Chelerythrine (LC Laboratories, Woburn, Mass.) is a highly specific PKC inhibitor which has been shown in culture to inhibit phosphorylation of specific PKC substrate (32) and was dissolved in DMSO. Equal volumes of pure DMSO was used in control dishes.

All luciferase transfections were done in the presence of cotransfected CMV-driven β-galactosidase pCMV-β; Clontech, Palo Alto, Calif.). The "full length" c-fos promoter luciferase plasmid, fos-lcf, has previously been described (77) and was a generous gift of Ron Prywes. This plasmid contains a 700 bp XhoI-NaeI sequence, including 40 bp 3' to the transcription start site. Deletion of the c-fos sequences renders the plasmid completely inactive with or without phorbol ester (not shown). The serum response element luciferase reporter $SRE_2$-basic was reconstructed from the $SRE_2$-CAT plasmid which was provided generously by Richard Treisman (58) The $SRE_2$-CAT construct is identical except that it contains in series two SRE's in inverse orientation, upstream of a tk-promoter, upstream of the luciferase gene. The blunt HindIII-XhoI fragment of the $SRE_2$-CAT was recloned into the blunt KpnI-XhoI site of $pGL_2$-basic luciferse reporter plasmid (Promega, Madison, Wisc.), placing the SRE's upstream of the tk-promoter. Transient transfections were carried out in RPMI-1640-HEPES with an ECM-600 electroporator (BTX, San Diego, Calif.) using 4 mm cuvettes at the following settings: V=200 v, R=720 Ω, C=3175 µF. Luciferase assays were done utilizing a commercially fit (Promega) and activity, expressed in arbitrary light units, was measured on a Pharmacia/Bio-Orbit 1251 as per manufacturer instructions. This activity is expressed as luciferase readings normalized to β-galactosidase. The β-galactosidase activity was assayed by calorimetric assay.

In the androgen independent cells, basal activity of the full-length c-fos promoter was elevated in comparison to that seen in LNCap cells (FIG. 1a). Basal levels were 47-, 35-, 4-, 8-, and 17-fold higher in TAC, PPC-1, DU145, ALVA-31, and MFM-M, respectively (FIG. 1a). This was associated with reduced sensitivity to phorbol ester. In the androgen dependent LNCap cells, c-fos promoter was inducible 256-fold by the phorbol ester phorbol 12-myristate 13 acetate ("PMA") (FIG. 1a). By contrast, in the androgen independent cells TAC, PPC-1, DU145, ALVA-31, and MFM-M the induction with PMA was 1.8-, 1.8-, 2.9-, 1.7-, and 1.6-fold, respectively. Elevated basal expression associated with noninducibility by phorbol ester is defined to indicate activation.

As with the c-fos promoter, SRE activity is relatively high in the androgen independent cells. Basal levels were 12-, 3.7-, 3-, 106-, and 13-fold higher than in LNCap in TAC, PPC-1, DU145, ALVA-31, and MFM-M, respectively (FIG. 1b). This was also associated with reduced sensitivity to phorbol ester. In the androgen dependent line LNCap, SRE was inducible 39-fold, whereas in the androgen independent cells TAC, PPC-1, DU145, ALVA311, and MFM-M it was inducible 3.8-, 2.8-, 1.7-, 1.1-, and 0.7-fold, respectively (FIG. 1b). Therefore, in the androgen independent cells, activation of the full-length c-fos promoter is associated with activation of the SRE.

EXAMPLE 2

Transient expression of c-fos promoter or SRE reporter plasmids was carried out in the presence of 5 g of Bluescript (0; negative control) or activated PKC (mPKC) or VP10SRF (V-SRF) expression plasmids, in addition to -galactosidase plasmid used to control for transfection efficiencies. The CMV-driven PKC plasmid encodes a rat PKC in which the pseudosubstrate region has been deactivated by an amino acid substitution, and was a generous gift of Peter Parker (25). This amino acid substitution renders the catalytic site free of intra-steric inhibition and thus raises its activity. The VP16-SRF plasmid has been described (27). This CMV-driven expression plasmid codes for a chimeric which includes the SRF DNA binding domain activated by the viral VP16 transactivation domain. As such it can activate the SRE without relying on phosphorylation pathways which typically are required (23). The PKC and VP16-SRF expression plasmids are based in different host vectors. The Bluescript plasmid which was used as a negative control in cotransfection experiments (Stratagene, LaJolla, Calif.), like the expression plasmids contains ampicillin resistance sequences and multiple cloning sites (FIG. 2).

Figure 2B:
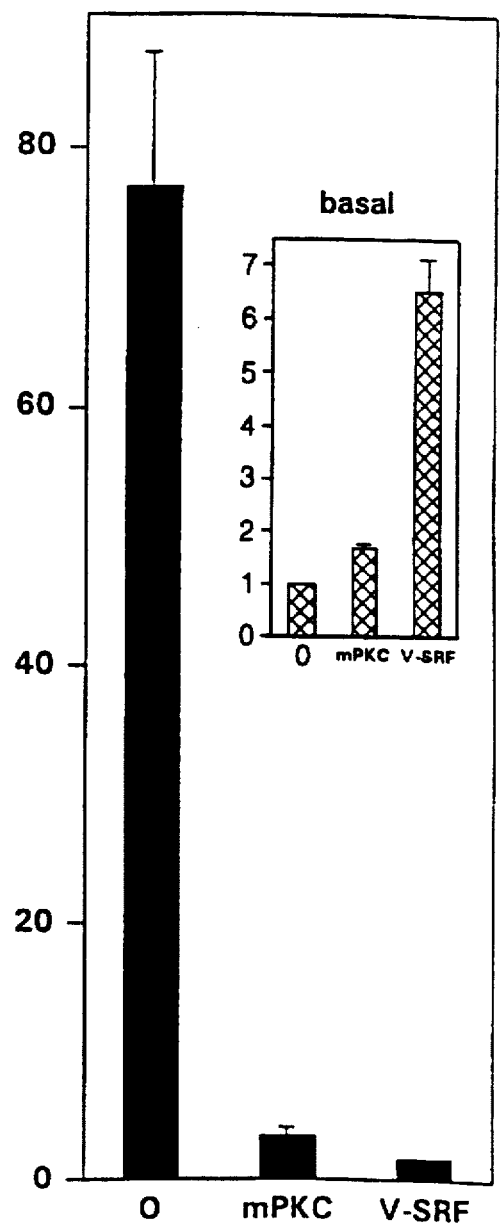

Expression of mPKC or VP16-SRF elevated basal c-fos promoter levels 21- and 18-fold, respectively (FIG. 2a). As in the spontaneous androgen independent cells, this was associated with highly significant reduction of phorbol ester inducibility (p<0.02), with reduction from 181-fold to 3.2- and 2.3 fold, respectively. SRE basal levels were elevated to 1.7- and 6.5-fold with mPKC and VP16-SRF, respectively and were also associated with highly significant reduction of phorbol ester inducibility (p<0.02), from 77- to 3.5 and 1.6-fold, respectively (FIG. 2b). These results imply that activation of non-PKC pathways may not be necessary for c-fos or SRE deregulation in androgen independence. The sufficiency of SRF activation in SRE activation suggests that PKC activation may be unnecessary for SRE activation in androgen independence. Likewise, it suggests that activation of an unknown number of mediators of the PKC signal may be sufficient to activate the SRE in androgen independent cells.

EXAMPLE 3

Transient expression of probasin reporter plasmid was carried out as described in example 1, with Bluescript, activated PKC (mPKC), or VP16-SRF (V-SRF). The androgen responsive PB-basic was constructed by recloning the probasin promoter into pGL$_2$-basic. To do so, the blunted BamHI-HindIII fragment of pBH500 (28); gift of Robert J. Matusik) was ligated into the blunted XhoI site of the pGL$_2$-basic and orientation was verified by restriction mapping. Cells were incubated in 10 nM mibolerone for 3 day and reporter assays were done as described in example 1.

As seen with effects on c-fos promoter or SRE, basal expression of probasin promoter was elevated 3.7- and 6.4-fold with mPKC and VP16-SRF, respectively. mPKC or VP16-SRF significantly (p<0.01) inhibited induction of probasin promoter by androgen, from 38- to 4.8- and 5.8-fold, respectively (FIG. 3). Thus, activation of PKC or SRF causes relatively androgen independent expression of at least one androgen target promoter.

EXAMPLE 4

PKC inhibitor chelerythrine selectively kills androgen independent cells. Cells were plated at subconfluence in 1% DCSS with or without 5 µM chelerythrine in DMSO. Control dishes received DMSO only. On day 5, dishes were visually inspected for morphological changes in cells growing in chelerythrine. In FIG. 4, representative fields are shown (120× magnification). ZR-75-1 reacted the same as LNCap, whereas DU145, ALVA-31, and MFM-M reacted the same as TAC and PPC-1 (not shown).

The hereinbelow list of references provides a complete citation of each of the references cited hereinabove. All of the references mentioned in the present application are incorporated in toto into this application by reference thereto.

References

1. Ponta, H., Cato, A. C. B., and Herrlich, p. (1992) Interface of pathway specific transcription factors. Bioch Biophys Acta, 1129:255–261.

2. Miner, J. N., Diamond, M. I., and Yamamoto, K. R. (1991) Joints in the regulatory lattice: Composite regulation by steroid receptor-Ap1 complexes. Cell Growth & Diff, 2:525–529.

3. Prins, G., Cooke, P. S., Birch, L., Donjacour, A. A., Yalcinkaya, T. M., Siiteri, P. K., and Cunha, G. R. (1992) Androgen receptor expression and 5α-reductase activity along the proximal-distal axis of the rat prostatic duct. Endocrinol, 130:3066–3073.

4. Lee, C. H., Sensibar, J. A., Dudek, S. M., Hiipakka, R. A., and Liao, S. (1990) Prostatic ductal system in rats; regional variation in morphological and functional activities. Biol. Rep, 43:1079–1086.

5. Sensibar, J. A., Griswold, M. D., Sylvester, S. R., Buttyan, R., Bardin, C. W., Cheng, C. Y., Dudek, S., and Lee, C. H. (1991) Prostatic ductal system in rats: regional variation in localization of an androgen-repressed gene product, sulfated glycoprotein-2. Endocrinol, 128:2091–2102.

6. Darbre, P. D., and King, R. J. B. (1987) progression to steroid insensitivity can occur irrespective of the presence of functional steroid receptors. Cell, 51:51–528.

7. Daly, R. J., and Darbre, P. D. (1990) Cellular and molecular events in loss of estrogen sensitivity in ZR-75-1 and T-47-D human breast cancer cells. Cancer Res, 50:5868–5875.

8. Katzenellenbogen, B. S., Kendra, K. L., Norman, M. J., and Berthois, Y. (1987) proliferation, hormonal responsiveness, and estrogen receptor content of MCF-7 human breast cancer cells grown in the short-term and long-term absence of estrogens. Cancer Res, 47:4355–4360.

9. Katz, A. E., Benson, M. C., Wise, G. J., Olsson, C. A., Bandyk, M. G., Sawczuk, I. S., Tomashefsky, P., and Buttyan, R. (1989) Gene activity during the early phase of androgen-stimulated rat prostate regrowth. Cancer Res., 49:5889–5894.

10. Pardee, A. B., (1989) G1 events and regulation of cell proliferation. Science, 246:603–608.

11. Muller, R. (1986) Cellular and viral fos genes: structure, regulation of expression, and biological properties of their encoded products. Bioch Biophys Acta, 823:207–225.

12. Herschman, H. R. (1991) primary response genes induced by growth factors and tumor promoters. Ann Rev Biochem, 60:281–319.

13. Greenberg, M. E., Siegfried, Z., and Ziff, E. B. (1987) Mutation of the c-fos gene dyad symmetry element inhibits serum inducibility of transcription in vivo and the nuclear regulatory factor binding in vitro. Mol. Cell Biol, 7:1217–1225.

14. Meyer, D. J., Stephenson, E. W., Johnson, L., Cochran, B. H., and Schwartz, J. (1993) The serum response element can mediate induction of c-fos by growth hormone. Proc Natl Acad Med USA, 90:6721–6725.

15. Williams, G. T., and Lau, L. F. (1993) Activation of the inducible orphan receptor gene nur77 by serum growth factors: dissociation of immediate-early and delayed-early responses. *Mol Cell Biol*, 13:6124–6136.

16. Alexandropoulos, K., Qureshi, S. A, Rim, M. Sukhatme, V. P., and Foster, D. A. (1992) v-Fps-responsiveness in the Egr-1 promoter is mediated by serum response elements. *Nucleic Acids Research*, 20:2355–2359.

17. Chavrier, P., Janssen-Timmen, U., Mattei, Marie-G., Zerial, M., Bravo, R., and Charnay, P. (1989) Structure, chromosome location, and expression of the mouse zinc finger gene Krox-20: multiple gene products and coregulation with the proto-oncogene c-fos. *Mol Cell Biol*, 9:787–797.

18. Fisch, T. M., Prywes, R., and Roeder, R. G. (1987) c-fos sequences necessary for basal expression and induction by epidermal growth factor, 12-o-tetradecanoyl phorbol-13-acetate and the calcium ionophore. *Mol Cell Biol*, 7:3490–3502.

19. Gilman, M. Z. (1988) the c-fos serum response element responds to protein kinase C-dependent and—independent signals but not to cyclic AMP. *Genes Dev*, 2:394–402.

20. Graham, R., and Gilman, M. (1991) Distinct protein targets for signals acting at the c-fos serum response element. *Science*, 241:189–192.

21. Fukumoto, Y., Kaibuchi, K., Oku, N., Hori, Y., and Takai, T. (1990). Activation of the c-fos serum-response element by the activated c-Ha-ras protein in a manner independent of protein kinase C and cAMp-dependent protein kinase. *J. Biol Chem*, 265:774–780.

22. Kaibuchi, K., Fukumoto, Y., Oku, N., Hori, Y., Yamamoto, T., Toyoshima, K., and Takai, Y. (1989) Activation of the serum-response element and 12-o-tetradecanoylphorbol-13-acetate response element by the activated c-raf-1 protein in a manner independent of protein kinase C. *J Biol Chem*, 264:20855–20858.

23. Treisman, R., (1992) The serum response element, *TIBS*, 17:423–426.

24. Shaw, P. E., Frasch, S., and Nordhiem, A. (1989) Repression of c-fos transcription is mediated through p67SRF bound to the SRE. *EMBO J*, 8:2567–2574.

25. Dekker, L. V, McIntyre, P., and Parker, P. J. (1993) Mutagenesis of the regulatory domain of rat protein kinase C-eta. A molecular basis for restricted histone kinase activity. *J Biol Chem*, 268:19498–19504.

26. Hipskind, R. A., and Nordheim, A. (1991) Functional dissection in vitro of the human c-fos promoter. *J Biol Chem*, 266:19583–19592.

27. Grueneberg, D. A., Natesan, S., Alexandre, C., and Gilman, M. Z. (1992) Human and drosophila homeodomain proteins that enhance the DNA-binding activity of serum response factor. *Science*, 257:1089–1095.

28. Rennie, P. S., Bruchovsky, N., Leco, K. J. Sheppard, P. C., McQueen, S. A, Cheng, H., Snoek, R., Hamel, A., Bock, M. E., MacDonald, B. S., Nickel, B. E., Chang, S., Liao, S., Cattini, P. A., and Matuski, R. (1993) Characterization of two cis-acting DNA elements involved in the androgen regulation of the probasin gene. *Mol Endrocrinol*, 7:23–36.

29. Rodriguez-Pena, A., and Rosengurt, E. (1984) Disappearance of Ca2+-sensitive, phospholipid-dependent protein kinase activity in phorbol ester-treated 3T3 cells. *Biochem Biophys Res Comm*, 120:1053–1059.

30. Frye, R. A. (1993) Involvement of G proteins, cytoplasmic calcium, phospholipases, phospholipid-derived second messengers, and protein kinases in signal transduction from mitogenic cell surface receptors. Chap. 14. In: Oncogenes and tumor suppressor genes in human malignancies. (Eds: Benz, C. C., and Liu, E. T.) *Kluwer Academic publishers, Boston*, 281–299.

31. Herbert, J. M., Augereau, J. M., Gleye, J., and Maffrand, J. P. (1990) Chelerythrine is a potent and specific inhibitor of protein kinase C. *Biochem Biophys Res Comm*, 172:993–999.

32. Venema, R. C., Raynor, R. L., Noland, T. A. J., and Kuo, J. F. (1993) Role of protein kinase C in he phosphorylation of cardiac myosin light chain 2. *Biochemical Journal*, 294: 401–406.

33. Wilson, J. D. (1992) Syndromes of Androgen Resistance. *Biol Rep.*, 46:168–173.

34. Sadi, M. V., Walsh, P. C., and Barrack, E. R. (1991) Immunohistochemical study of androgen receptor in metastatic prostate cancer; comparisons of receptor content and response to hormonal therapy. *Cancer*, 67:3057–3064.

35. Ruizfeld de Winter, J. A., Trapman, J., Brinkmann, A. O., Boersma, W. J. A., Mulder, E., Schroeder, F. H., Classen, E., and van der Kwist, T. (1990) Androgen receptor heterogeneity in human prostatic carcinomas visualized by immunochemistry. *J Pathol*, 161:329–332.

36. van Aubel, O. G., Bolt-de Vries, J., Blanenstein, M. A., de Jong, F. H., and Schroder, F. H. (1989) Circulating testosterone, prostatic nuclear androgen receptor and time to progression in patients with metastatic disease of the prostate treated by orchiectomy. *Urol Res*, 17:99–102.

37. Chodak, G. W., Krane, D. M., Py, L. A., Takeda, H., Johnson, K., and Chang, C. (1992) Nuclear localization of androgen receptor in heterogeneous samples of normal, hyperplastic and neoplastic human prostate. *J Urol*, 147:798–803.

38. Sadi, M. V., and Barrack, E. R. (1993) Image analysis of androgen receptor immunostaining in metastatic prostate cancer- Heterogeneity as a predictor of response to hormonal therapy. *Cancer*, 71:2574–2580.

Van Der Kwast, T. H., Schalken, J., Ruizeveld De Winter, J. A., Van Vroonhoven, C. C. J., Mulder, E., Boersma, W., and Trapman, J. (1991) Androgen receptors in endocrine-therapy-resistant human prostate cancer. *Int J Cancer*, 48:189–193.

40. Newmark, J. R., Hardy, D. O., Tonb, D. C., Carter, B. S., Epstein, J. I. Issacs, W. B., Brown, T. R., and Barrack, E. R. (1992) Androgen receptor gene mutations in human prostate cancer. *proc Natl Acad Med USA*, 89:6319–6323.

41. Schonenberg, M. P., Hakimi, J. M., Wang, S., Bova, G. S., Epstein, J. I., Fishbeck, K. H., Isaacs, W. B., Walsh, P. C., and Barrack, E. R. (1994) Microsatellite mutation (CAG24–18) in the androgen receptor gene in human prostate cancer. *Biochem Biophys Res Comm*, 198:74–80.

42. Culig, Z., Hobisch, A., Crornauer, M. V., Cato, A. C. B., Hittmair, A., Radmayr, C., Eberle, J., Bartsch, G., and Klocker, H. (1993) Mutant androgen receptor detected in an advanced stage prostatic carcinoma is activated by adrenal androgens and progesterone. *Mol Endocrinol*, 7:1541–1550.

43. Shemshedini, L., Knauthe, R., Sassone-Corsi, P., Pornon, A., and Gronemeyer, H. (1991) Cell-specific inhibitory and stimulatory effects of Fos and Jun on transcription activation by nuclear factors. *EMBO J*, 1:3839–3849

44. Minty, A., and Kedes, L. (1986) Upstream regions of the human cardiac action gene that modulate its transcription in muscle cells: presence of an evolutionarily conserved repeated motif. *Mol Cell Biol*, 6:2125–2136.

45. Boxer, L. M., Prywes, R., Roeder, R. G., and Kedes, L. (1989) The sarcomeric actin CArG-binding factor is indistinguishable from the c-fos serum response factor. Mol Cell Biol, 9:515–522.

46. Mohun, T. J., Chambers, A. E., Towers, N., and Taylor, M. V. (1991) Expression of genes encoding the transcription factor SRF during early development of Xenopus Laevis: identification of a CArG box-binding activity as SRF. *EMBO J*, 10:933–940.

57. Seshadri, T., and Campisi, J. (1990) Repression of c-fos transcription and an altered genetic program in senescent human fibroblasts. *Science*, 247:205–209.

48. Rodriguez, P. A., and Rozengurt, E. (1984) Disappearance of Ca2+sensitive, phospholipid-dependent protein kinase activity in phorbol ester-treated 3T3 cells. *Biochem Biophys Res Comm*, 120:1053–1059.

49. Fabbro, D., Kung, W., Costa, S. D., Borner, C., Regenass, U., and Eppenberger, U. (1991): Involvement of protein kinase C in the growth regulation of human breast cancer cells. Chap. 12. In: Genes, oncogenes, and hormones: Advances in cellular and molecular biology of breast cancer, (Eds. Dickson, R. B., and Lippman, M. E.) *Kluwer Academic publishers, Boston*, 229–248.

50. Coughlin, S. R., Lee, W. M. F., Williams, P. W., Giels, G. M., and Williams, L. T. (1985) c-myc gene expression is stimulated by agents that activate protein kinase C and does not account for the mitogenic effect of PDGF. *Cell*, 43:243–251.

51. Helper, J. R., Earp, H. S., and Harden, T. K. (1993) Long-term phorbol ester treatment down-regulates protein kinase C and sensitizes the phosphoinositide signaling pathway to hormone and growth factor stimulation. Evidence for a role of protein kinase C in agonist-induced desensitization. *J. Biol Chem*, 263:7610–411.

52. Battistone, M. J., Padilla, G. M., and Petrow, V. (1993) 1-Dehydro-melengestrol acetate inhibits the growth and protein kinase C activity of androgen-independent Dunning rat prostatic tumors. *Cancer Chemother Pharmacol*, 31:407–411.

53. Yoshimasa, T., Sibley, D. R., Bouvier, M., Lefkowitz, R. J. and Caron, M. G. (1987) Cross-talk between cellular signalling pathways suggested by phorbol-ester-induced adenylate cyclase phosphorylation. *Nature*, 327:67–70.

54. Yan, G., Fukabori, Y., Nikolaropoulos, S., Wang, F., and McKeehan, W. L. (1992) Heparin-binding keratinocyte growth factor is a candidate stromal to epithelial cell andromedin. *Mol Endocrinol*, 6:2123–2128.

55. Chung, L. W. K. (1993) Implications of stromal-epithelial interaction in human prostate cancer growth, progression and differentiation. *Sem. Can. Biol.*, 4:183–192.

56. Eldar, H. Zisman, Y., Ullrich, A., and Livneh, E (1990) Over expression of protein kinase C α-subtype in Swiss/3T3 fibroblasts causes loss of both high and low affinity receptor numbers for epidermal growth factor. *J Biol Chem*, 265:13290–13296.

57. Gauthier-Rouviere, C., Cai, Q. Q., Lautredou, N., Fernandez, A., Blanchard, J. M., and Lamb, N. J. (1993) Expression and purification of the DNA-binding domain of SRF; SRF-DB, a part of a DNA-binding protein which can act as a dominant negative mutant in vivo, *Exp Cell Res*, 209:208–215.

58. Hill, C. S., Marais, R., John, S., Wynne, J., Dalton, S., and Treisman, R. (1993) Functional analysis of a growth factor-responsive transcription factor complex. *Cell*, 73:395–406.

59. Koelle, M. R., Talbot, W. S., Segraves, W. A., Bender, M. T., Cherbas, P., and Hogness, D. S. (1991) The Drosophila EcR gene encodes an ecdysone receptor, a new member of the steroid receptor superfamily. *Cell*, 67:59–77.

60. Christopherson, K. S., Mark, M. R., Bajaj, V., and Godowski, P. J. (1992) Ecdysteroid-dependent regulation of genes in mammalian cells by a Drosophila ecdysone receptor and chimeric transactivators. *Proc Nat Acad Med USA*, 89:6314–6318.

61. Thomas, H. E., Stunnenberg, H. G., and Stewart, (1993) A.F. Heterodimerization of the Drosophila ecdysone receptor with retinoid X receptor and ultraspiracle. *Nature*, 362:471–475.

62. Yao, Tso-P., Forman, B. M., Jiang, Z., Cherbas, L., Chen, J. D., McKeown, M., Cherbas, L., and Evans, R. M. (1993) Functional ecdysone receptor is the product of EcR and Ultaspiracle genes. *Nature*, 366:476–479.

63. Gualberto, A. et al. (1992) *Mol. Cell. Biol.* 12:4209–14.

64. Tilley, W. D., Wilson, C. M., Marcelli, M., and McPhaul, M. J. (1990) Androgen receptor gene expression in human prostate carcinoma cell lines. *Can Res*, 50:5382–5386.

65. Sonnenschein, C., Olea, N., Pasanen, M. E., and Soto, A. M. (1989) Negative controls of cell prliferation: human prostate cancer cells and androgens. *Can Res*, 49:3474–3481.

66. Wolf, D. A., Schulz, P., and Fittler, F. (1991) Synthetic androgens suppress the transformed phenotype in the human prostate carcinoma cell line LNCap. *British Journal of Cancer*, 4:47–53.

67. van Steenbrugge, G. J., van Uffelen, C. J. C., Bolt, J., and Schroder, F. H. (1991) The human prostatic cancer cell line LNCap and its derived sublines: an in vitro model for the study of androgen sensitivity. *J. Ster Biochem Mol Biol*, 40:207–214.

68. Lin, T., Sonnenschein, C., and Soto, A. M. (1991) proliferative patterns of androgen-resistant human prostate cell variants. *Endocrinol*, 73 Annual Meeting:abstract 552.

69. Krongrad, A., Wilson, C. M., Wilson, J. D., Allman, D. R., and Mcphaul, M. J. (1991) Androgen increases androgen receptor protein while decreasing receptor mRNA in LNCap cells. *Mol Cell Endocrinol*, 76:79–88.

70. Loop, S. M., Rozeanski, T. A., and Ostenson, R. C. (1993) Human primary prostate tumor cell line, ALVA-31: A new model for studying the hormonal regulation of prostate tumor cell growth. *Pros*, 22:93–108.

71. Brothman, A. R., Wilkins, P. C., Sales, E. W., and Somers, K. D. (1991) Metastatic properties of the human prostatic cell line, PPC-1, in athymic nude mice. *J. Urol*, 145:1088–1091.

72. Brothman, A. R., Lesho, L., Somers, K. D., Wright, G. L. J., and Merchant, D. J. (1989) phenotypic and cytogenetic characterization of a cell line derived from primary prostatic carcinoma. *Int J Cancer*, 44:898–903.

73. Chen, T. R., (1993) Chromosome identify of human prostate cancer cell lines, PC-3 and PPC-1, *Cytogenet Cell Genet*, 62:183–184.

74. Hackenberg, R., Luttchens, S., Hofmann, J., Kunzmann, R., Holzel, F., and Schulz, Klaus-D. (1991) Androgen Sensitivity of the New Human Breast Cancer Cell Line MFM-223, MFM-223. *Can Res*, 51:5722–5727.

75. Hackenberg, R., Hawighorst, T., Filmer, A., Slater, E. P., Bock, K., Beato, M., and Schulz, Klaus-D. (1992)

Regulation of androgen receptor mRNA and protein level by steroid hormones in human mammary cancer cells. *J. Steroid Biochem. Molec. Biol,* 43:599–607.

76. Labrie, F., Simard, J., de Launoit, Y., Poulin, R., Theriault, C., Dumont, M., Dauvois, S. (1992) Martel, C., and Li, S. Androgens and breast cancer. *Cancer Detec. Preven.* 16:31–38.

77. Medema, R. H., Wubbolts, R., and Bos, J. L. (1991) Two dominant inhibitory dutants of p21ras interfere with insulin-induced gene expression. *Mol Cell Biol,* 11:56963–5967.

I claim:

1. A method of selectively inhibiting growth or proliferation of hormone independent cancer cells in a cell population wherein said cells originate from hormone dependent cancer cells, said method comprising treating the cell population with an effective amount of at least one protein kinase C inhibiting agent, wherein the hormone independent cells are hormone independent prostate cancer cells contained in a population of prostate cancer cells or the hormone independent cells are hormone independent breast cancer cells contained in a population of breast cancer cells and wherein the PKC inhibitor is chelerythrine.

2. A method of selectively inhibiting growth or proliferation of hormone independent cancer cells in a cell population wherein said cells originate from hormone dependent cancer cells, said method comprising treating the cell population with an effective amount of an agent such that activation of the serum response element (SRE) is inhibited, wherein the hormone independent cells are hormone independent prostate cancer cells contained in a population of prostate cancer cells or the hormone independent cells are hormone independent breast cancer cells contained in a population of breast cancer cells and wherein the PKC inhibitor is chelerythrine.

* * * * *